United States Patent [19]
Hege

[11] 3,987,138
[45] Oct. 19, 1976

[54] INERT CARRIER MIXING PROCESS

[75] Inventor: Douglas W. Hege, Woodland Hills, Calif.

[73] Assignee: Hege Advanced Systems Corporation, Huntington Beach, Calif.

[22] Filed: Apr. 6, 1972

[21] Appl. No.: 241,765

[52] U.S. Cl. ............... 264/117; 23/313 R; 426/285; 426/442; 259/1 R
[51] Int. Cl.$^2$ .............................. B01J 2/00
[58] Field of Search ............ 99/DIG. 4; 23/313; 264/117; 426/285, 442; 259/1 R

[56] References Cited
UNITED STATES PATENTS

| | | | |
|---|---|---|---|
| 2,515,880 | 7/1950 | Douglas et al. | 252/135 |
| 2,900,256 | 8/1959 | Scott | 99/DIG. 4 |
| 3,221,338 | 11/1965 | Segal | 99/DIG. 4 |
| 3,396,034 | 8/1968 | Blondheim | 99/DIG. 4 |
| 3,609,088 | 9/1971 | Sumner | 23/313 X |

*Primary Examiner*—Joseph M. Golian

[57] ABSTRACT

This application is directed to processes involving the use of nonmiscible inert liquid carriers such as halogenated hydrocarbons. The processes are applicable to mixing, agglomerating, coating, dyeing, reorientating, crystallizing, precipitating, reacting and similar types of operations. Examples of products which can be treated by these processes are foods, pharmaceuticals, detergents, fabrics and papers. The inert carrier acts as an expanded matrix to support and disperse such products to facilitate carrying out the indicated operating steps.

16 Claims, 1 Drawing Figure

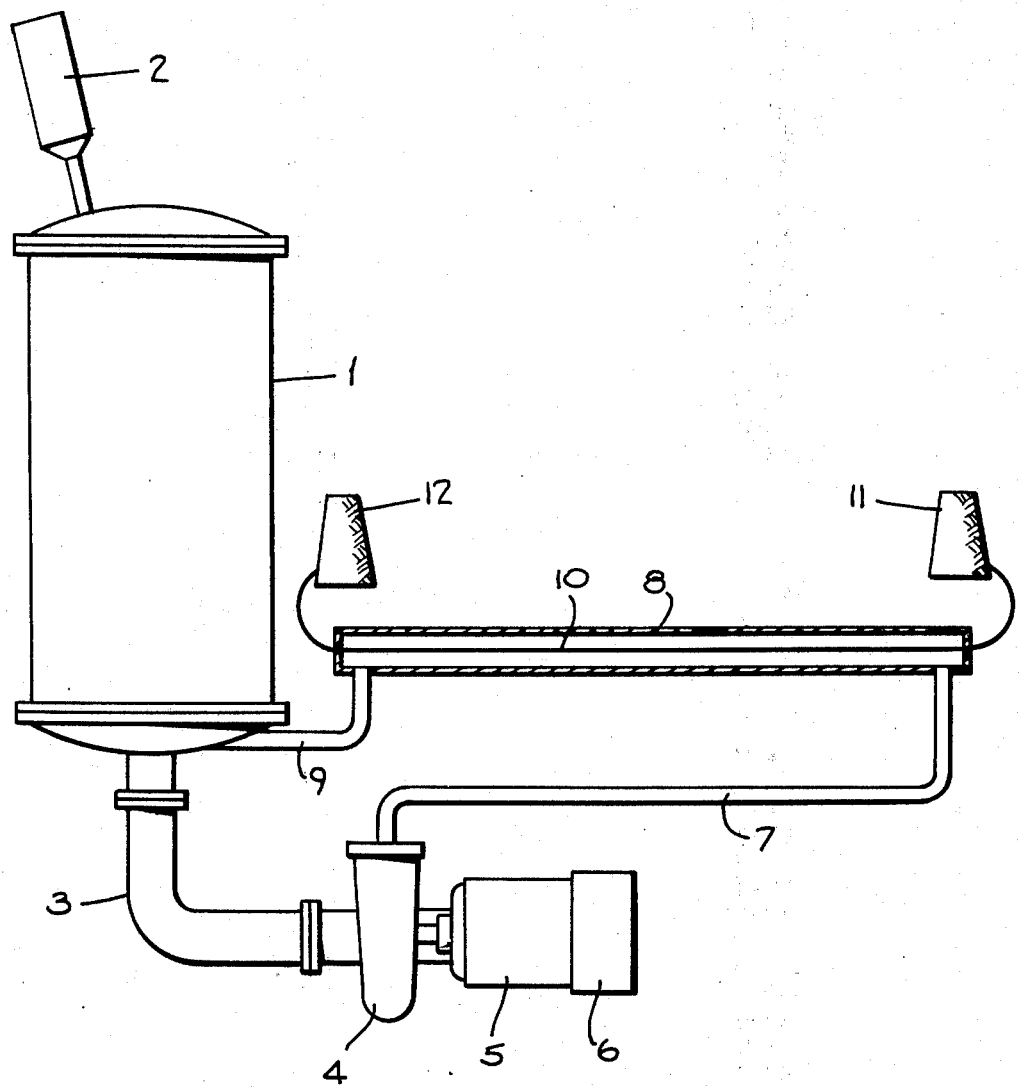

INERT CARRIER MIXING PROCESS

THE INVENTION

This invention is directed to the process of treating a substance in the presence of an inert liquid carrier. The carrier serves as an expanded matrix which supports the substance to be treated and thereby facilitates the desired result, which may be mixing, agglomeration, coating, reorientation, dyeing, reaction, etc.

The process of this invention is useful for mixing, agglomerating, crystallizing, or precipitating one or more ingredients or compounds when one or more of the ingredients have been dispersed in a substantially nonmiscible liquid carrier, maintaining a suspension or dispersion by turbulent mixing, and subsequently separating the final product from the liquid carrier.

Cocoa and sugar can be agglomerated by this method by using minor amounts of water in the agglomeration process. For example, if a mixture of 20 grams cocoa and 80 grams sugar is added to a jet mixing device containing between about 2–10 grams water and 750–1500 grams of Freon 12 (at 50 psig) the mixture will agglomerate. The agglomeration is accomplished within a few seconds of mixing. This process can be used for the agglomeration of sugar by itself or with diverse substances, such as fruit juice components or mixtures, natural or synthetic, milk solids, and gelatins. Another embodiment is to add 100 grams of a powdered instant coffee and 5 grams of $H_2O$ to about 500 grams of Freon 113. After thorough mixing the agglomerated particles are separated from the liquid and dried. The agglomerated particles had a darker and richer color than the original powdered coffee. A similar process can be used to agglomerate other food substances such as milk solids and fruit juice concentrates. In place of the Freon 12, other fluorinated or fluorochlorinated hydrocarbons (lower alkanes, i.e. one to four carbon atoms) can be used which are commercially available, such as Freon 113 and 114. The process can be carried out at atmospheric pressure or an elevated pressure in liquid phase, which is primarily dictated by the vapor pressure of the inert carrier material and the temperature of the mixture. The water, or other suitable wetting agent, serves as the agglomerating agent. Only a minor amount of the wetting agent should be used; this is readily determined experimentally and normally is about from 1 to 10% by weight based upon the weight of the solids used. This process is also useful for agglomerating many other substances, such as pharmaceuticals and detergents. For example, aspirin (25 mg), a low molecular weight alcohol such as ethanol or isopropanol (25–75 grams) and Freon 318 (150 grams) were mixed at atmospheric pressure and 22° F to agglomerate the aspirin. In another example 100 grams of anhydrous sodium tripolyphosphate, 60cc $H_2O$, and 500–750 grams Freon 113, were mixed at atmospheric pressure, 70° F. The water was added to the anhydrous sodium tripolyphosphate in two stages of 30cc each. An agglomerated product was obtained which readily dissolved in water.

Each of these examples is characterized by the use of a nonsolvent Freon and normally a minor amount of a solvent, such as water or alcohol. The procedure is to mix the solvent and nonsolvent and to add the solids to the liquids. The entire mixture is then subjected to high speed agitation for several seconds and then filtered and dried. Alternatively, the solids may be added to the nonsolvent and the solvent can then be added. It is preferable not to initially mix the solids and solvents together since this leads to uneven agglomerates which must then be broken and reduced to uniform size which is a more difficult procedure.

The mixing device can be of conventional construction such as a tumbling device or a higher energy mixer containing a jet mixing device.

A preferred embodiment of the present invention is to place the liquid/solid mixture after agglomeration on a fine screen which retains the solids and permits the liquid to pass into a collecting tray below the screen. The tray-screen combination is then vibrated by a conventional vibrating device such as a Syntron Model BFO12, made by FMC. This assists in obtaining the proper sizing and/or separating of the agglomerate particles. The liquid separates from the solid by flowing through the screen to a collection and recirculation device. This procedure has been used to remove 95% of the carrier within a few seconds.

Another embodiment of this invention is a process of depositing when one of the ingredients dispersed in the nonmiscible liquid carrier will deposit itself on one of the other ingredients, or upon a shape or body within the vessel in which they are contained.

Dioctylsodiumsulphosuccinate (DSS by American Cyanamid) has been coated onto cocoa by this method. The coating was carried out in a Freon carrier in a high energy-blender mixer. About 100 grams cocoa was added to about 1000 grams Freon and 8 grams of an alcohol solution containing 50% DSS was added to the Freon and cocoa. After a few seconds mixing the cloudy solution was filtered to separate the cocoa. No agglomeration occurs under this procedure. The product is then dried. The final product dissolves or disperses more readily in water.

In an Excedrin P.M. brand composition the methapyrilene component reacts with certain of the other components and forms a tablet having a mottled appearance. It is therefore desirable to coat the methapyrilene to render it inert. Methapyrilene, about 100 grams, about 50 grams of a gelatin solution containing about 50% gelatin, and a blue dye were added to a container with about 750–1000 grams Freon 114 and the constituents mixed for several seconds. The entire solid mass rose to the top of the Freon and was separated and dried. It was virtually dry upon completion of the process and then was allowed to air dry. The methapyrilene was uniformly coated with the gelatin. The coated methapyrilene can then be mixed with the other ingredients of Excedrin PM and successfully tableted.

This process is also useful for coloring substances. About 100 grams of starch were added to 500 grams of Freon 114. A fraction of a percent of U.S. certified food coloring was added to the mixture and after thorough agitation the starch was uniformly colored.

A furter embodiment of this invention is the process of orientating or interlocking fibers (such as paper pulp) where one or more ingredients are stirred under conditions using a substantially nonmiscible liquid carrier, forming a dispersion or dispersions of each, slurry mixing said dispersions and separating the carrier from the orientated or interlocked composition or fibers.

A dry sulphite paper pulp (about 50 grams) was mixed with Freon 113 (about 250 grams) in a high energy mixer-blender. The resultant mixture was passed through a fine-mesh screen and the pulp residue left on the screen had the appearance of cotton puffs.

The pulp as then rolled by a conventional technique to form a sheet of paper.

The above procedure was repeated in which 5–20% water was added to the pulp-Freon mixture. The fluid was then subjected to high energy mixing. The product was filtered through a fine-mesh screen and the pulp residue was rolled into a sheet of paper.

Finished paper products, particularly newspaper, may be treated by the above techniques to reconstitute the paper for further use.

Another embodiment of this invention is the process of dyeing cloth, thread, etc., by mixing compositions of one or more ingredients one of which is a dyeing agent using a substantially nonmiscible liquid carrier, forming dispersions thereof, flowing such dispersions over and through fabrics or threads, and then separating the dispersions from the fabrics or thread, and finally separating the dyeing agent from the nonmiscible liquid carrier.

The conventional solvent dyeing of textiles can be carried out with chlorinated hydrocarbons such as perchloroethylene and possibly trichloroethylene. However, this technique requires the chemical modification of conventionally used dyes since most dyes are not very soluble in solvents. This may be accomplished by converting ionic, acid or basic dyes to organic soluble forms. The present invention is directed to the use of nonsolvent dyes. For example conventional water-soluble dyes, in concentrations of 1/2% in Freon 12 and Freon 114, can be used. The dye in an aqueous solution may be added to the inert Freon carrier. For example, U.S. certified food color dyes of 2.5% in water may be used as commercially available. Alternatively, a water-insoluble dye can be used in a water medium. In the dyeing operation when a cloth is to be dyed it can be maintained between screens; a pulsing of the pressure of the medium improves the penetration and dispersion of the dye throughout the textile.

The dyeing process of this invention may be carried out in any suitable mixing device. An embodiment of a preferred apparatus is shown in FIG. 1. The liquid ingredients are added to the container 1 through liquid dispenser 2. The liquid mixture is drawn from container 1 through conduit 3 by the action of centrifugal pump 4, driven by motor 5 and variable speed drive 6. The liquid mixture is pumped through conduit 7 into the dyeing tube 8 and back into the container through return conduit 9. The contents of the container are thus continuously recirculated by these means. The thread 10 to be dyed is unwound from bobbin 11 through tube 8 and back onto bobbin 12. At each end of the dyeing tube 8, seal members of conventional design (not shown) are used.

The amount of inert carrier used in the above processes can be widely varied and may comprise from about 25 to 99.5% of the mixture. For example in the dyeing process only a very minor amount of dye in a solution, from 0.5 to 20%, is used whereas in agglomerating the amount of inert carrier is normally about 50–95% of the mixture.

This invention has been described in terms of specific embodiments set forth in detail. Alternative embodiments will be apparent to those skilled in the art in view of this disclosure, and accordingly such modifications are to be contemplated within the spirit of the invention as disclosed and claimed herein.

I claim:
1. The process which comprises adding at least two substances, one of which is a solid and one of which is a solvent for the solid, in a liquid carrier which is inert, immiscible, and insoluble with respect to said substances, turbulently mixing said substances and said liquid until said substances interact and separating said substances from said liquid.

2. The process of claim 1 wherein said liquid carrier is a halogenated hydrocarbon.

3. The process of claim 1 wherein said solvent is water.

4. The process of claim 1 wherein said substances comprise a solid and a liquid which is a wetting agent for said solids and mixing said substances and said liquid carrier until said solids are agglomerated.

5. The process of claim 4 wherein said solid is a powdered detergent.

6. The process of claim 4 wherein said solid is a food stuff.

7. The process of claim 4 wherein said solid is a pharmaceutical.

8. The method of agglomerating solids to produce a substance which is readily dispersed in a liquid which comprises
   subjecting to turbulent mixing a mixture of (1) said solids, (2) a minor amount of a wetting agent for said solids, and (3) an inert halogenated hydrocarbon which is immiscible with said wetting agent and in which said solid is insoluble, wherein said mixture is prepared by:
   A. mixing (1) and (3) and then adding (2); or
   B. mixing (2) and (3) and then adding (1), and separating said solids and wetting agent from said mixture.

9. The process of claim 8 wherein said halogenated hydrocarbon is a fluorochlorinated hydrocarbon.

10. The process of claim 9 wherein said wetting agent is water.

11. The process of claim 10 wherein said solid is a powdered detergent.

12. The process of claim 8 wherein said wetting agent is water and said solid is a food stuff.

13. The process of claim 8 wherein said solid is a pharmaceutical.

14. The process of claim 13 wherein said wetting agent is a low molecular weight alcohol, said halogenated hydrocarbon is a fluorinated hydrocarbon and said pharmaceutical is aspirin.

15. The process of claim 12 wherein said foodstuff is selected from the group consisting of sugar, cocoa, coffee, dried fruit juice concentrate and milk solids, wherein the ratio of said foodstuff to water is about 100:1–10.

16. The method of agglomerating solids to produce a substance which is readily dissolved in water which comprises:
   subjecting to turbulent mixing a mixture of (1) said solids, (2) a minor amount of water, and (3) fluorochlorinated hydrocarbon, wherein said mixture is prepared by:
   A. mixing (1) and (3) and then adding (2); or
   B. mixing (2) and (3) and then adding (1),
   separating the wetted solids from said mixture and drying said solids.

* * * * *

UNITED STATES PATENT AND TRADEMARK OFFICE
CERTIFICATE OF CORRECTION

PATENT NO. : 3,987,138
DATED : October 19, 1976
INVENTOR(S) : Douglas W. Hege

It is certified that error appears in the above-identified patent and that said Letters Patent are hereby corrected as shown below:

Col. 2, line 57, delete "furter" and substitute --further--.

Col. 3, line 1, delete "as" and substitute --was--.

Signed and Sealed this

Twenty-first Day of December 1976

[SEAL]

Attest:

RUTH C. MASON
*Attesting Officer*

C. MARSHALL DANN
*Commissioner of Patents and Trademarks*